(12) United States Patent
Smolak et al.

(10) Patent No.: US 10,539,497 B2
(45) Date of Patent: Jan. 21, 2020

(54) AUTOMATED ALIGNMENT OF OPTICS WITHIN A FLOW CYTOMETER

(71) Applicant: Essen Instruments, Inc., Ann Arbor, MI (US)

(72) Inventors: Andrew W. Smolak, Golden, CO (US); Erica Dawson Tenent, Broomfield, CO (US); Kathy L. Rowlen, Longmont, CO (US); Garrett S. Wilson, Erie, CO (US); Christopher H. Converse, Boulder, CO (US); Evan M. Toth, Boulder, CO (US)

(73) Assignee: Essen Instruments, Inc., Ann Arbor, MI (US)

( * ) Notice: Subject to any disclaimer, the term of this patent is extended or adjusted under 35 U.S.C. 154(b) by 394 days.

(21) Appl. No.: 15/315,698

(22) PCT Filed: Jun. 2, 2015

(86) PCT No.: PCT/US2015/033803
§ 371 (c)(1),
(2) Date: Dec. 1, 2016

(87) PCT Pub. No.: WO2015/187708
PCT Pub. Date: Dec. 10, 2015

(65) Prior Publication Data
US 2017/0115203 A1    Apr. 27, 2017

Related U.S. Application Data

(60) Provisional application No. 62/008,371, filed on Jun. 5, 2014.

(51) Int. Cl.
*G01N 15/14* (2006.01)
*G01N 21/64* (2006.01)

(52) U.S. Cl.
CPC ..... *G01N 15/1436* (2013.01); *G01N 21/6428* (2013.01); *G01N 2021/6439* (2013.01)

(58) Field of Classification Search
CPC .......... G01N 15/1434; G01N 15/1459; G01N 2015/1006; G01N 21/6428; G01N 2021/6439; G01N 15/1436
(Continued)

(56) References Cited

U.S. PATENT DOCUMENTS

| 3,516,629 A | 6/1970 | Say |
| 3,758,058 A | 9/1973 | Neudeck et al. |

(Continued)

FOREIGN PATENT DOCUMENTS

| EP | 0822404 A2 | 2/1998 |
| EP | 1002968 A2 | 5/2000 |

(Continued)

*Primary Examiner* — Rebecca M Fritchman
(74) *Attorney, Agent, or Firm* — Marsh Fischmann & Breyfogle LLP

(57) ABSTRACT

A method and a flow cytometer system in which a light path is aligned to optimally direct light from a light source to a flow cell of a flow cytometer instrument are provided. The flow cytometer may include an orientable mirror disposed in the light path between the light source and the flow cell. By changing an orientation of the mirror through a sequence of different orientations, an optimal orientation of the mirror may be determined, and the mirror may be oriented accordingly before proceeding to conduct a flow cytometry investigation.

18 Claims, 12 Drawing Sheets

(58) Field of Classification Search
USPC .......................................................... 436/52
See application file for complete search history.

(56) References Cited

U.S. PATENT DOCUMENTS

| | | | |
|---|---|---|---|
| 4,857,451 | A | 8/1989 | Schwartz |
| 5,386,962 | A | 2/1995 | Adriance |
| 5,736,105 | A | 4/1998 | Astle |
| 8,482,731 | B2 | 7/2013 | Muraki |
| 2003/0235919 | A1 | 12/2003 | Chandler |
| 2006/0038989 | A1 | 2/2006 | Domack |
| 2012/0070818 | A1 | 3/2012 | Rowlen |
| 2012/0217914 | A1 | 8/2012 | Mawhinney |
| 2013/0050782 | A1 | 2/2013 | Heng |
| 2013/0080082 | A1* | 3/2013 | Howes .................... G01N 15/14 702/49 |
| 2013/0327957 | A1* | 12/2013 | Ayliffe .................... G01N 21/64 250/459.1 |
| 2015/0132766 | A1 | 5/2015 | Yasuda et al. |

FOREIGN PATENT DOCUMENTS

| | | |
|---|---|---|
| EP | 1176412 A2 | 1/2002 |
| WO | 2008010120 A2 | 1/2008 |
| WO | 2009093017 A1 | 7/2009 |
| WO | 2013147114 A1 | 10/2013 |

* cited by examiner

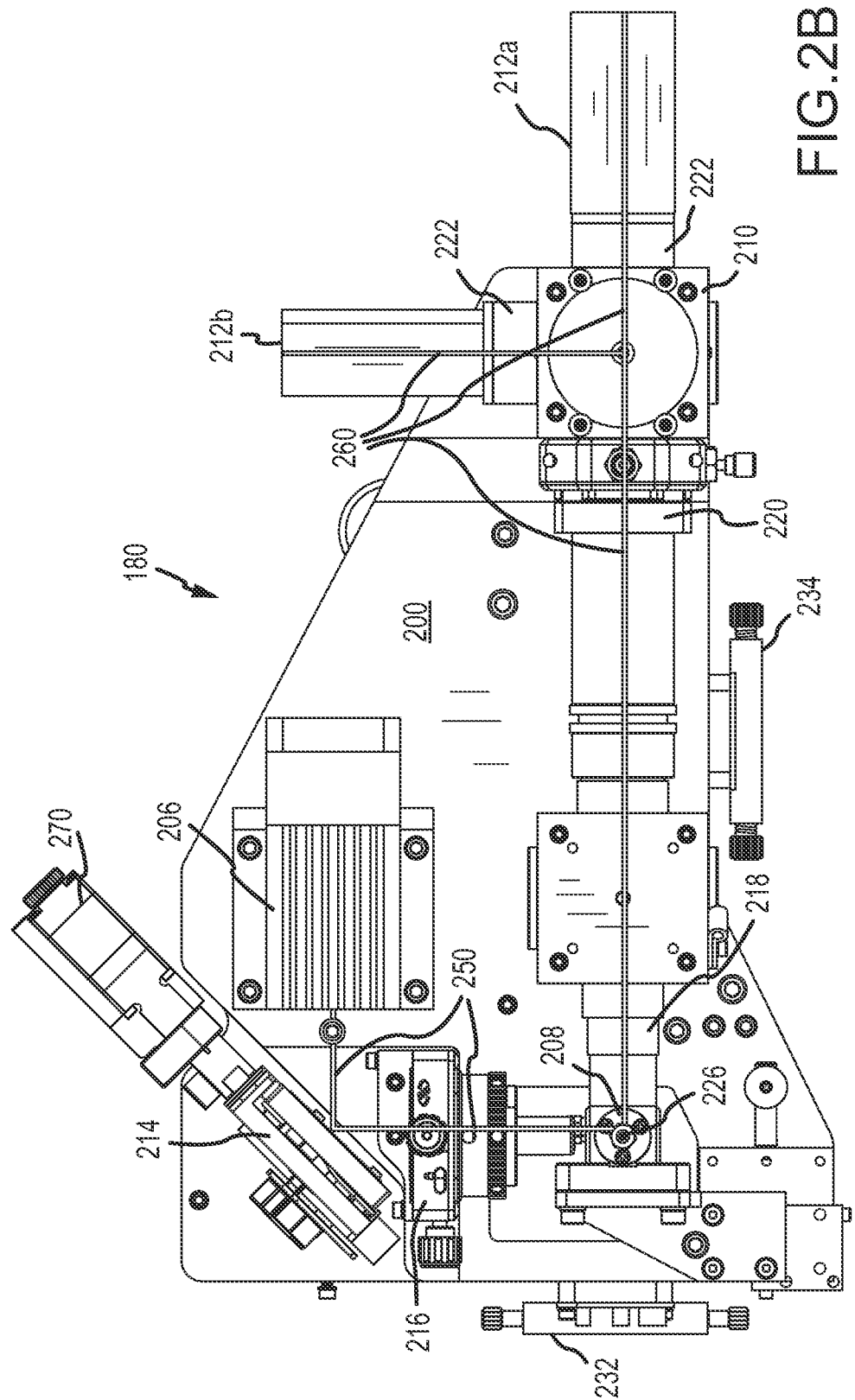

AUTOMATED ALIGNMENT OF OPTICS WITHIN A FLOW CYTOMETER

CROSS-REFERENCE TO OTHER APPLICATIONS

This application is related to a concurrently filed international patent application under the Patent Cooperation Treaty entitled "FLOW CYTOMETER WITH OPTICAL SYSTEM ASSEMBLY" filed with the U.S. Patent and Trademark office as receiving office, assigned international application number PCT/US2015/033795, and this application is related to U.S. provisional patent application entitled "FLOW CYTOMETER WITH OPTICAL SYSTEM ASSEMBLY" filed Jun. 5, 2014, assigned application Ser. No. 62/008,401, the entire contents of each such referenced application being incorporated herein by reference. This application also claims the benefit of U.S. provisional patent application Ser. No. 62/008,371 entitled "AUTOMATED ALIGNMENT OF OPTICS WITHIN A FLOW CYTOMETER" filed Jun. 5, 2014, the entire contents of which are incorporated herein by reference.

FIELD OF THE INVENTION

This disclosure relates to flow cytometry, including flow cytometry devices and related methods.

BACKGROUND OF THE INVENTION

Flow cytometry is an analytical technique used in a number of applications to measure physical and/or chemical properties of biological or non-biological particles as they flow in a sample fluid through an investigation cell, commonly referred to as a flow cell. Although the sample fluid may be investigated by subjecting the sample fluid to a variety of stimuli, light is one common stimulus technique. Scattered light exiting from the flow cell may be detected and analyzed to provide information on the characteristics of particles present in the sample fluid. Light stimulation and light detection techniques may be tailored to identification of particular characteristics indicative of the presence of particular types of particles. For example, one technique is to stain a sample fluid with one or more stains (also referred to as dyes) that associate with a particular biological component of interest. The stains may have fluorescent activity that provides a fluorescent emission about a particular wavelength, the detection of which provides an indication of the presence of that biological component. For example, two different fluorescent stains, one that associates with protein and another that associates with nucleic acid, may aid in the detection of virus particles. Light detection may be designed to specifically detect light at the different fluorescent emission wavelengths of different stains. This may involve splitting light received from the flow cell into different light wavelength ranges, such as using a dichroic mirror that passes some wavelengths of light while reflecting other wavelengths of light.

Devices for performing flow cytometry are referred to as flow cytometers. Flow cytometers are often designed to optimize detection of a specific type of particle, for example specific cells, bacteria or virus. A complicating issue for flow cytometer robustness and durability over a prolonged period is that flow cytometers tend to be very sensitive instruments that require very precise alignment of optical elements for optimal performance. Flow cytometry optical elements, which may include a light source, a flow cell, lenses, beam splitters and light detectors, are typically precisely located and secured in place in the flow cytometer with a desired alignment within and protected by a protective enclosure, or shell. To provide some ability to fine-tune alignment of the delivery of light to the flow cell, a light source, such as a laser, may be mounted on an adjustable mount that permits some adjustment of the positioning and orientation of the light source to permit some fine-tuning of the alignment with the flow cell or with a lens disposed between the light source and the flow cell. Furthermore, achieving best results during a flow cytometry investigation requires proper the alignment of various optical components of the flow cytometer instrument and a hydrodynamically focused sample stream within the flow cell assembly for optimal sample excitation and emission collection.

SUMMARY OF THE INVENTION

Accordingly, a method and a flow cytometer system in which a light path is optimally aligned to direct light from a light source to a flow cell of a flow cytometer instrument are provided. In this regard, the flow cytometer may include an orientable mirror disposed in the light path between the light source and the flow cell. By changing an orientation of the mirror through a sequence of different orientations, an optimal orientation of the mirror may be determined. Since vibration, thermal expansion and contraction, and other forces that may effect the alignment of various optical components in the flow cytometer instrument can continue to negatively impact optimal performance of the flow cytometer during its useful product life, the optimal orientation of the mirror may be re-determined and reset by periodically determining a current optimal orientation of the mirror and setting the mirror accordingly prior to performing further flow cytometry investigations.

In one aspect, a method of aligning a light path to direct light from a light source to a flow cell of a flow cytometer instrument may include setting an orientation of an orientable mirror disposed to direct light from the light source toward the flow cell. Setting an orientation of the orientable mirror may include, starting with the mirror positioned at a first test orientation, changing positioning of the mirror from the first test orientation through a sequence of different test orientations of the mirror. The method may also include, for each test orientation of the sequence, flowing a validation fluid through the flow cell while the light source is operating to provide light to the mirror and collecting flow cytometry response data on light emitted from the flow cell with the mirror at the test orientation. In this regard, the validation fluid may comprise a known concentration of at least one known particle. The method may further include analyzing the flow cytometry response data to identify an optimal orientation of the mirror from among each of the test orientations of the mirror. The method may additionally include orienting the mirror at a set orientation corresponding to the identified optimal orientation.

In a further aspect, a flow cytometer system may include a flow cell, a light source, a light path to direct light from the light source to the flow cell, an orientable mirror disposed in the light path that directs light from the light source into the flow cell, at least one detector that detects light from the flow cell, and a control processor. The control processor may be operable to, starting with the mirror positioned at a first test orientation, control the mirror to change positioning of the mirror from the first test orientation through a sequence of different test orientations of the mirror. The control processor may also be operable to, for each test orientation of the mirror, control flowing of a validation fluid through the flow cell while the light source is operating to provide light to the mirror and collecting flow cytometry response data on light emitted from the flow cell with the mirror at the said test orientation. In this regard, the validation fluid may comprise a known concentration level of at least one known particle. The control processor may further be operable to analyze the flow cytometry response data to identify an optimal orientation of the mirror from among each of the test orientations of the mirror. The control processor may additionally be operable to control the mirror to be at a set orientation corresponding to the identified optimal orientation.

Various refinements exist of the features noted in relation to the various aspects of the present invention. Further features may also be incorporated in the various aspects of the present invention. These refinements and additional features may exist individually or in any combination, and various features of the various aspects may be combined. These and other aspects and advantages of the present invention will be apparent upon review of the following Detailed Description when taken in conjunction with the accompanying figures.

DESCRIPTION OF THE DRAWINGS

FIGS. 2A-2D are perspective, top and end views of one embodiment of a flow cytometer internal assembly that may be included within the flow cytometer instrument of FIGS. 1A-1B.

DETAILED DESCRIPTION

Figure 1A:
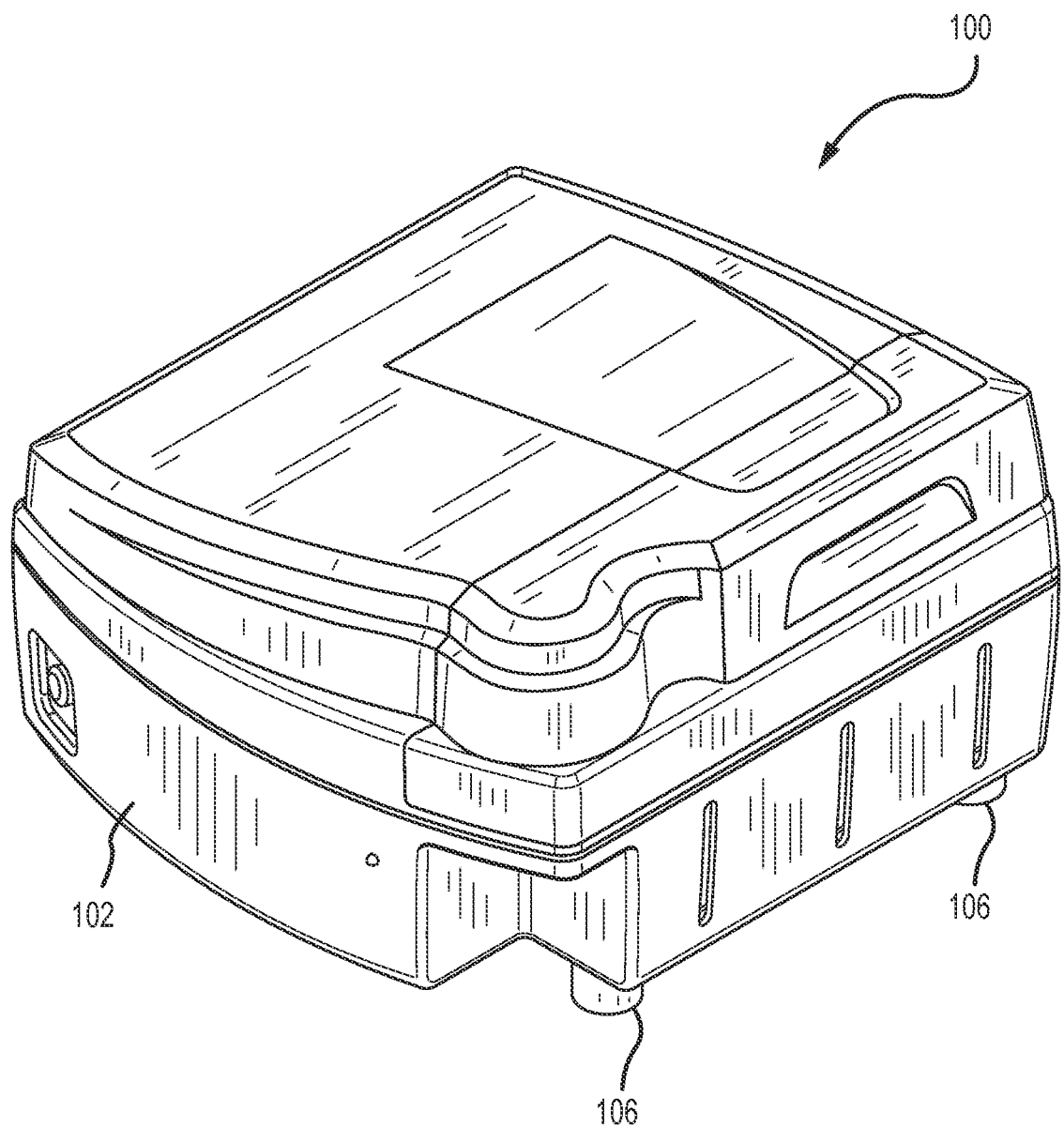
FIGS. 1A-1B are perspective and side views of one embodiment of a flow cytometer instrument.
Figure 1B:
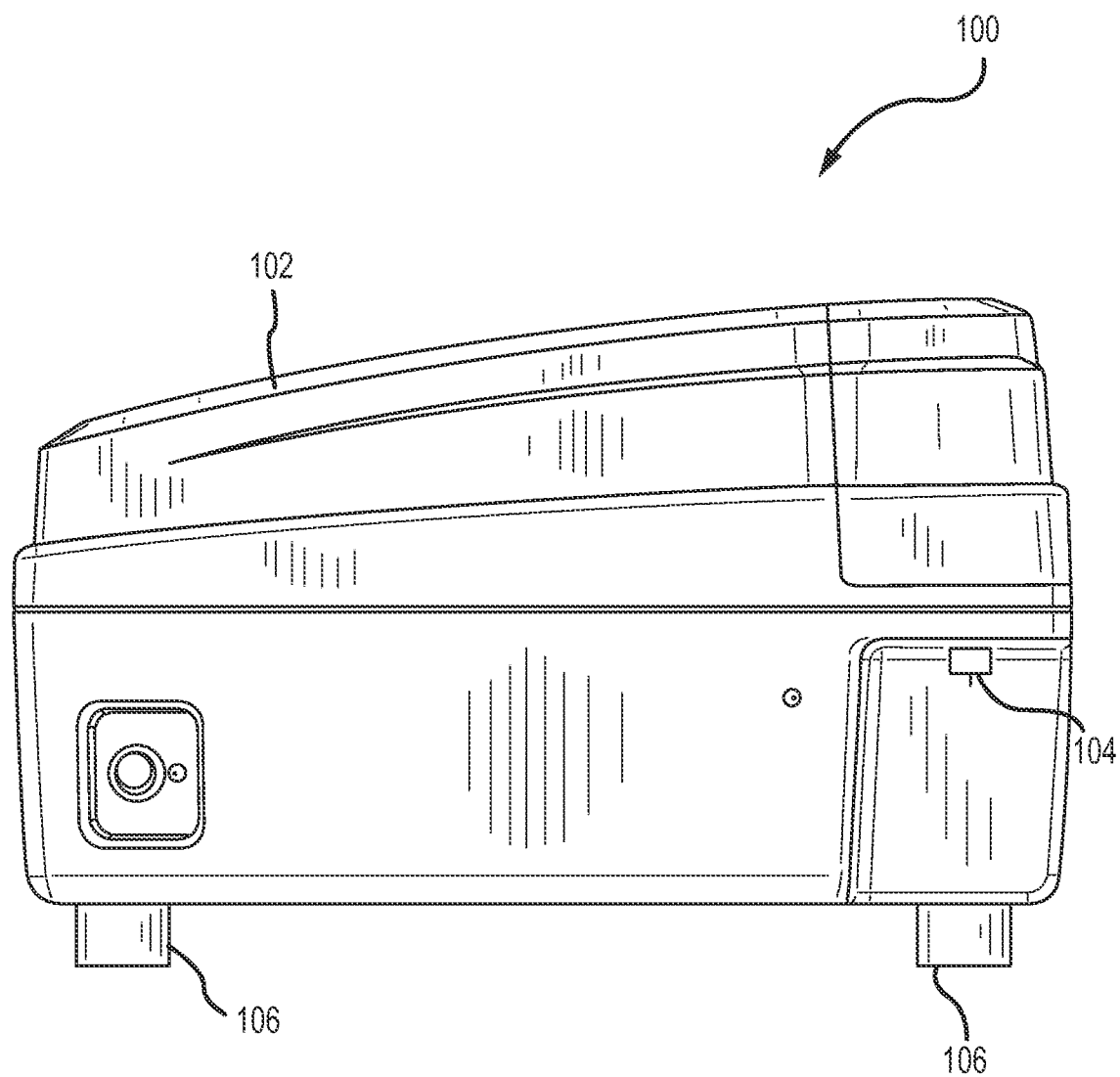

FIGS. 1A-1B show a flow cytometer 100 that includes flow cytometry componentry contained within a protective enclosure 102. Fluid samples may be introduced into the flow cytometer 100 for flow cytometry investigation through a sample inlet 104. The flow cytometer 100 includes support pads 106 on which the weight of the enclosure 102 and contents within the enclosure 102 are supported. Advantageously, the support pads 106 may be of a material that provides significant vibration isolation to the enclosure 102, and to contents within the enclosure 102, from ambient environment vibrations that may be transmitted through a shelf, table or other surface on which the flow cytometer 100 may be situated during use. The support pads 106 may, therefore, provide a vibration isolation structure that provides a vibration propagation barrier to the enclosure 102 and contents within the enclosure 102. For example, the support pads 106 may be of a polymeric composition that provides a vibration decomposing effect. Example polymeric compositions include thermoplastic and thermoset polymer compositions.

Figure 2A:
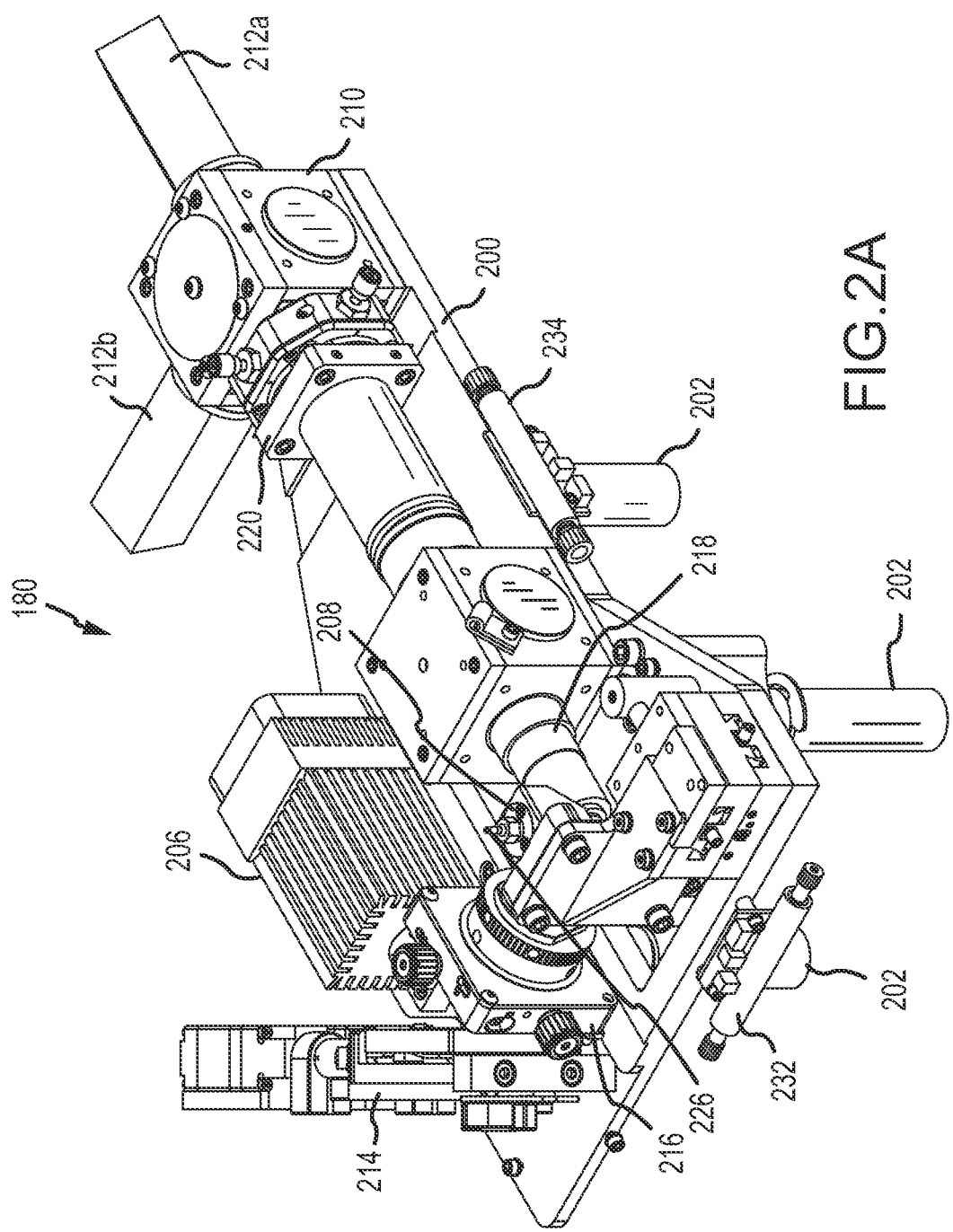
Figure 2C:
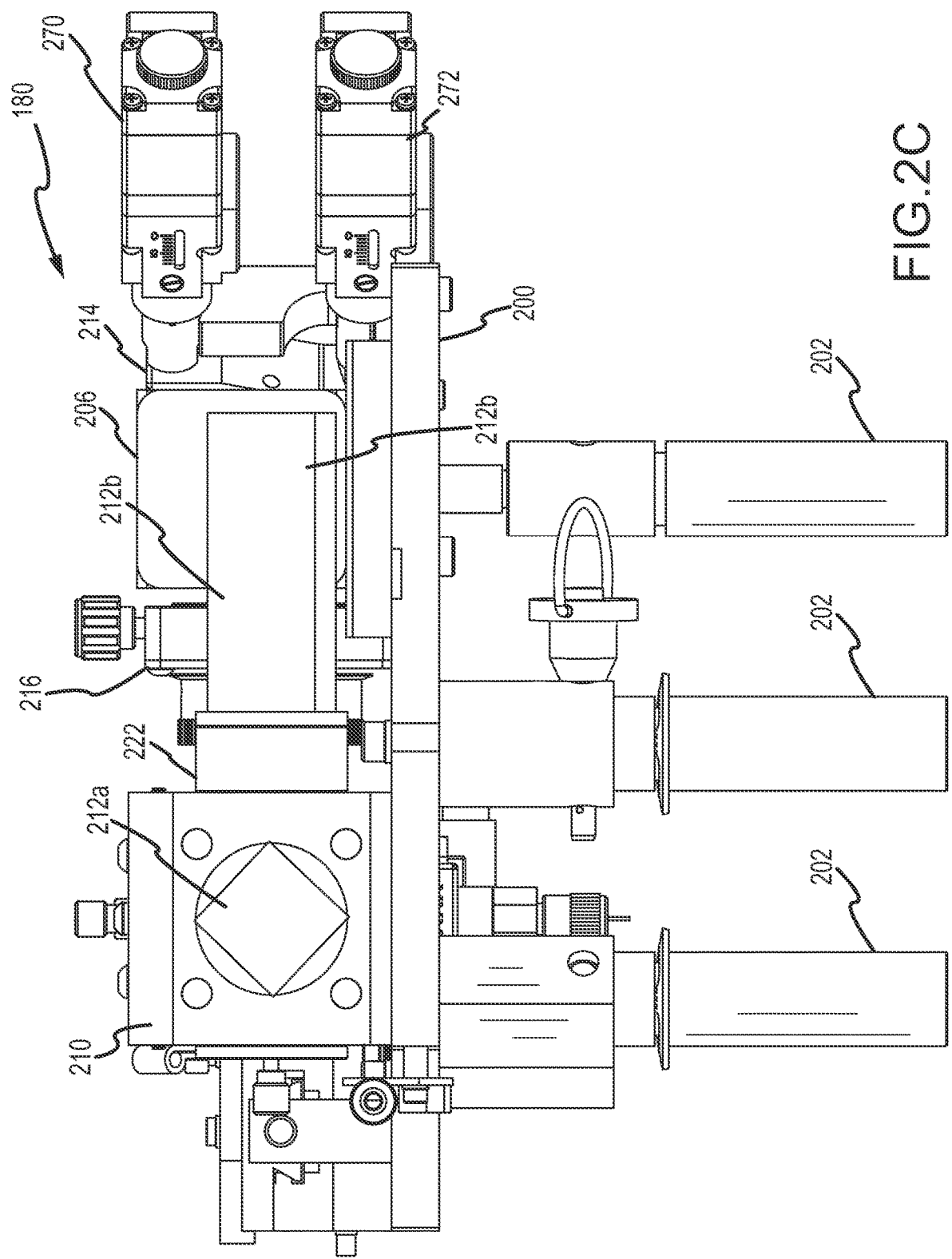
Figure 2D:
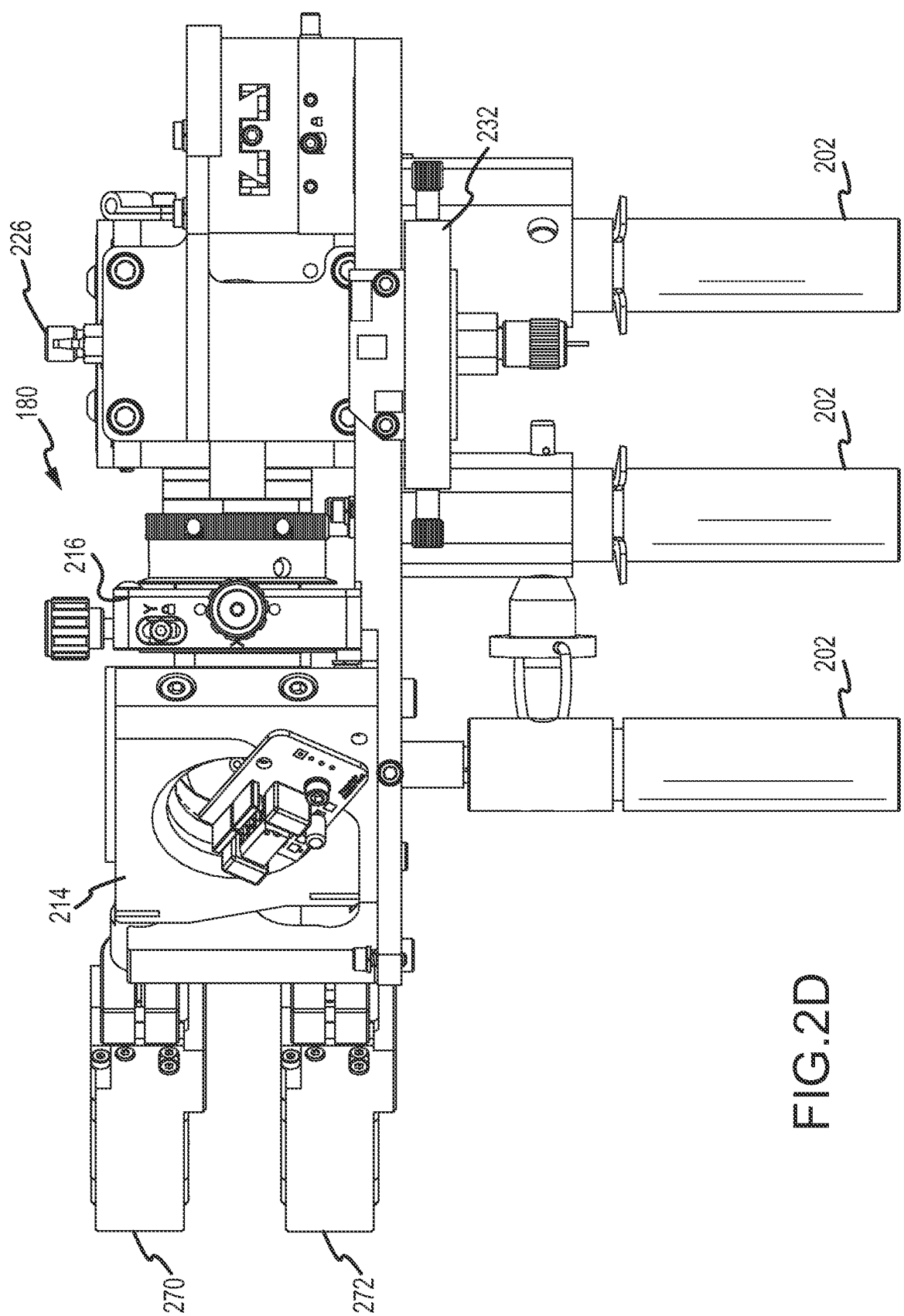

FIGS. 2A-2B show an example flow cytometer internal assembly 180 that may be disposed within the enclosure 102 of the flow cytometer 100. The internal assembly 180 includes a flow optical system assembly including support platform 200 and a number of flow cytometry optical components supported by the support platform 200, with the optical components having fixed relative positioning configured for performing flow cytometry investigations of sample fluids. The flow cytometry optical system assembly is supported by a support structure including three rigid support members 202 and vibration isolation mounts (not shown in FIGS. 2A-2B) that are supported by the support members 202, and on which the entire weight of the support platform 200 and components supported by the support platform 200 are supported during flow cytometry investigation operations.

The flow cytometry optical components supported by the support platform 200 include a light source in the form of a laser unit 206, a flow cell unit 208 and a light detection system including a dichroic mirror unit 210 and two light detector units 212, for example which may include photo-multiplier tubes. During operation of a flow cytometry investigation of sample fluid flowing through an investigatory flow path of a flow cell of the flow cell unit 208, light from the laser unit 206 travels along a first optical path 250 to the flow cell. The first optical path 250 includes a mirror unit 214 that includes an orientable mirror that reflects light from the laser unit 206 to direct that light through a focusing lens 216 to focus light in the vicinity of the investigatory flow path within the flow cell of the flow cell unit 208. Orientation of the mirror of the mirror unit 214 may be controlled by operating one or both of a pair of motors 270, 272 coupled to the mirror. Light from the investigatory flow path of the flow cell is directed along a second optical path 260 from the flow cell to the dichroic mirror unit 210 for detection by the light detectors 212. The second optical path 260 includes a focusing lens unit 218 and a spatial lens unit 220 between the flow cell unit 208 and the dichroic mirror unit 210. A dichroic mirror within the dichroic mirror unit 210 splits the light between light that passes through the dichroic mirror and is directed toward light detector 212a and light that is reflected by the dichroic mirror and is directed toward light detector 212b. Band-pass filters 222 may be disposed in the optical paths to the light detectors 212 to pass a narrow light including a wavelength or band of wavelengths targeted for detection by the respective light detectors 212a, 212b.

During operation of the flow cytometer 100 to perform a flow cytometry investigation of a fluid sample, the fluid sample to be investigated may be introduced into the flow cytometer through the sample inlet 104. The sample fluid is conducted to an inlet (not shown in FIGS. 2A-2B) to the flow cell unit 208. The sample fluid flows through the investigatory fluid path in the flow cell unit 208 and exits the flow cell unit 208 through a sample exit 226. Sample fluid introduced into the flow cell unit 208 through the sample fluid inlet flows through a transparent section of the flow cell unit 208 where it is subjected to incident light from the laser unit 206 and exits through the sample exit 226. The investigatory flow path passes through the transparent section. The transparent section may, for example, be made of a quartz crystal material. Between the sample inlet 104 of the flow cytometer 100 and the inlet to the flow cell unit 208, the fluid sample passes through a fluid path (not shown) that includes a flow meter 232 where the flow rate of the fluid sample may be measured for data collection purposes as part of a feedback control mechanism for controlling the fluid sample flow rate to the flow cell unit 208. In the flow cell unit 208, a sheath fluid is introduced around the fluid sample flow before the fluid sample flows through the transparent section for investigation. The sheath fluid is introduced into the flow cell unit 208 through a sheath fluid inlet (not shown in FIGS. 2A-2B). Prior to introduction of the sheath fluid into the flow cell unit 208, the sheath fluid passes through a fluid path (not shown in FIGS. 2A-2B) that includes a flow sensor 234 for monitoring of the sheath fluid flow rate to the flow cell unit 208 and for use for feedback control to control the flow rate of the sheath fluid to the flow cell unit 208. The flow sensors 232 and 234 are conveniently supported on the support platform 200.

Figure 3A:
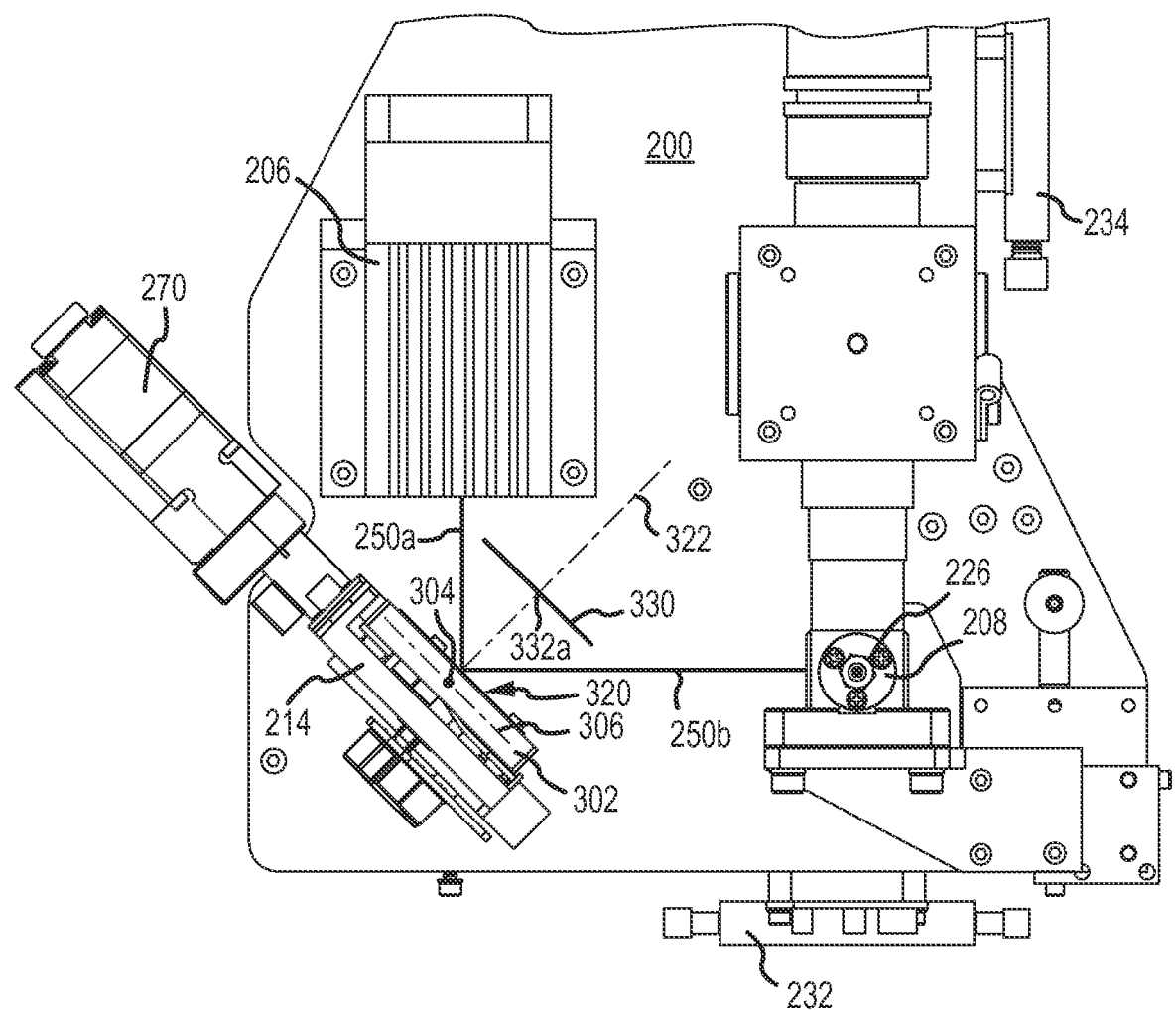
FIG. 3A-3C are enlarged top views of a portion of the internal assembly of FIGS. 2A-2D.
Figure 3B:
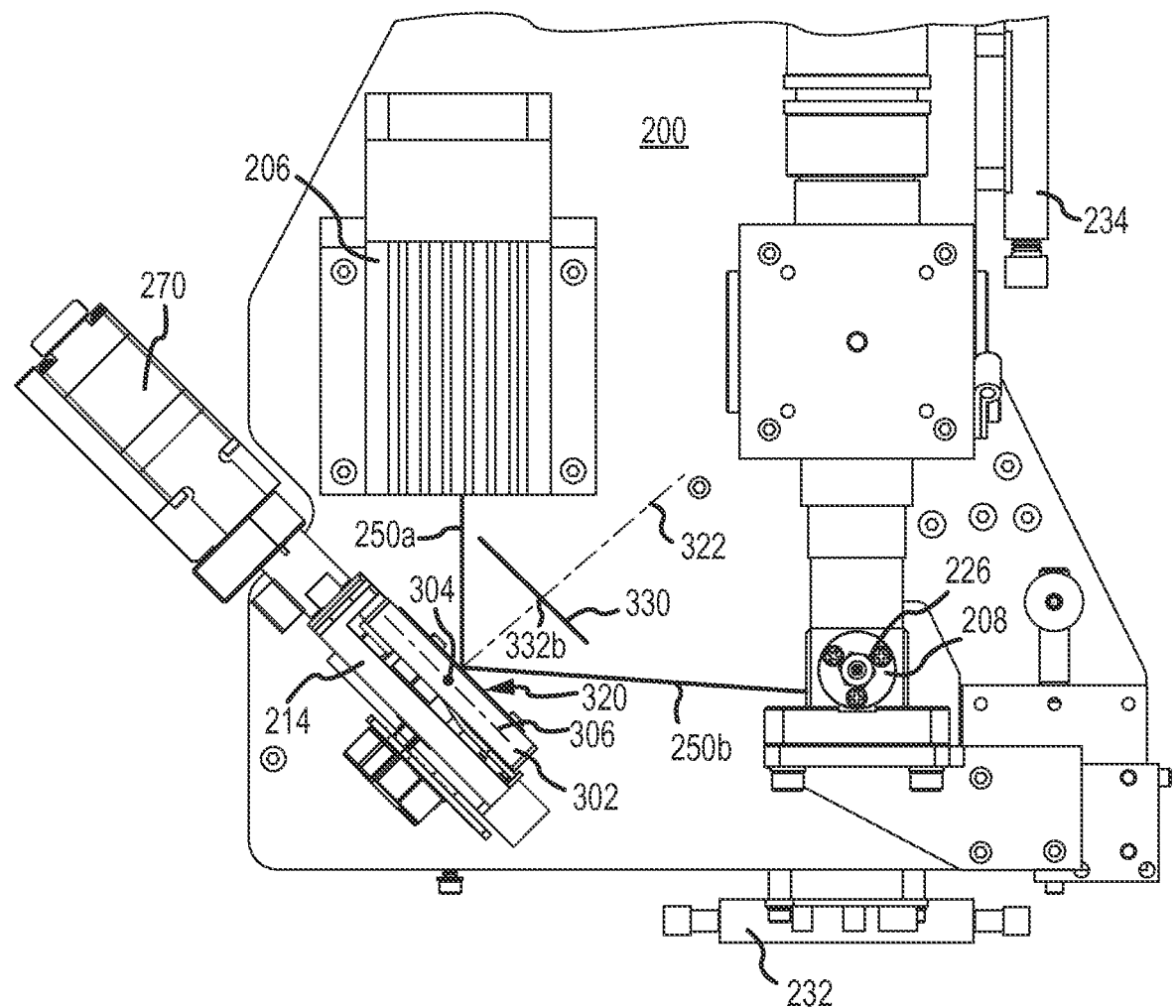
Figure 3C:
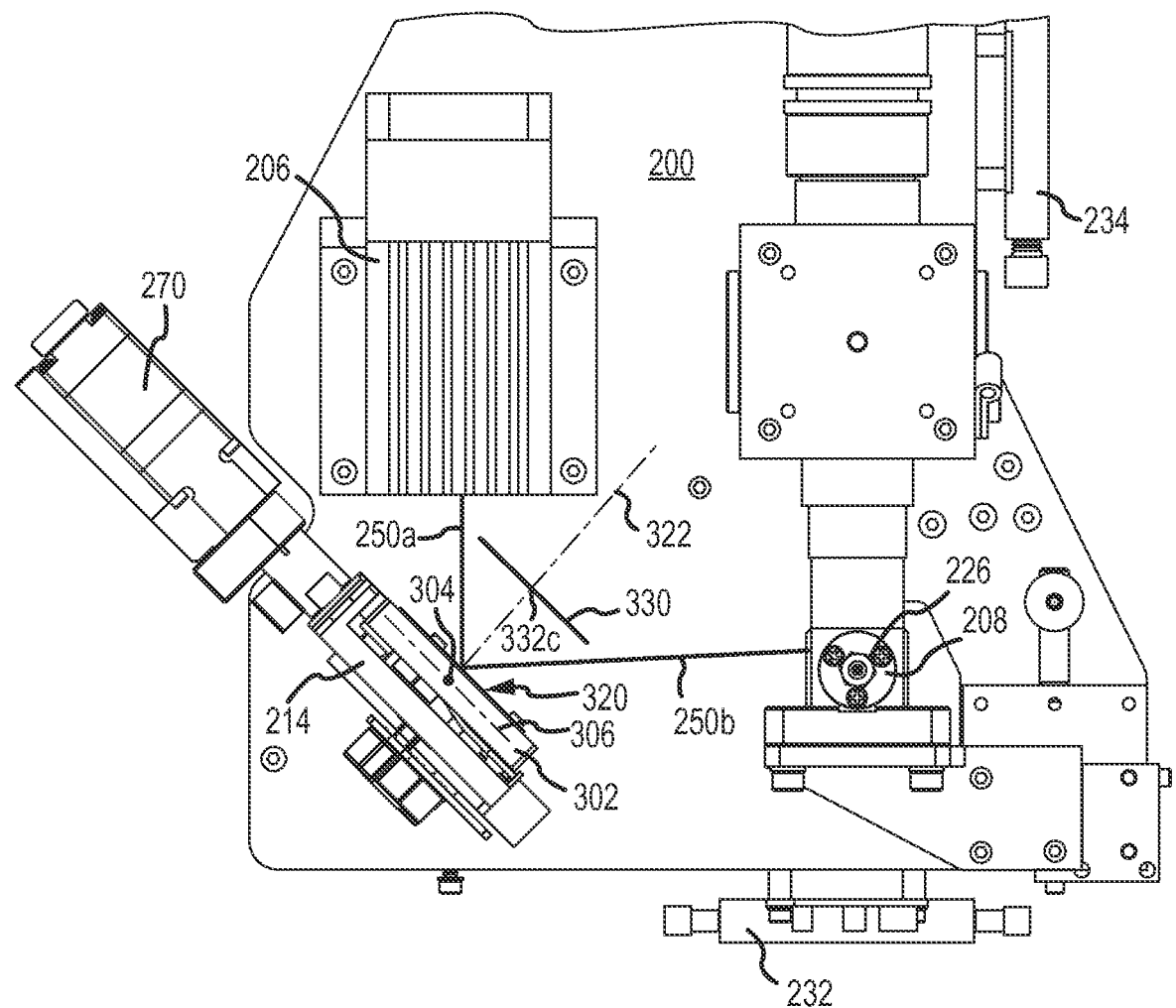

FIGS. 3A-3C show more detailed views of the optical assembly 180 including the mirror unit 214 that is disposed in the first optical path 250 between laser unit 206 and the focusing lens 216. In FIGS. 3A-3C, some components of the optical assembly 180 that may be in the first optical path 250 such as the focusing lens 216 are not shown. The mirror unit 214 includes an orientable mirror 302. The orientable mirror 302 may be oriented in a plurality of different orientations. In this regard, the orientable mirror 302 may be rotatable around two axes 304, 306 of rotation in order to achieve each different orientation. The two axes 304, 306 around which the mirror 302 rotates may be orthogonal and one may be referred to herein as the tip axis 304 and the other may be referred to herein as the tilt axis 306.

The pair of motors 270, 272 may be coupled to the mirror 302 and are operable to cause rotation of the mirror around the tip and tilt axes 304, 306 in order to orient the mirror 302 in each of its different orientations. In this regard, the motors 270, 272 may be linear stepper motors, and in order to provide sufficient resolution between different mirror 302 orientations, each step of each motor 270, 272 may correspond to no more than 300 nanometers of linear motion.

The mirror 302 includes a reflective surface 320, and the mirror 302 is positioned in the first optical path 250 so that the reflective surface 320 thereof faces the laser unit 206 and the flow cell unit 208 in order to reflect light from the laser unit 206 to the flow cell of the flow cell unit 208 (e.g., via an intermediary focusing lens). In this regard, the reflective surface 320 of the mirror 302 divides the first optical path 250 into a portion 250A from the laser unit 206 to the mirror 302 and a portion 250B from the mirror 302 to the flow cell of the flow cell unit 208.

A central axis 322 of the mirror 302 extends perpendicular to the reflective surface 320 thereof and intersects an imaginary plane 330 that is transverse to the portion 250B of the first optical path 250 between the mirror 302 and the flow cell of the flow cell unit 208. In each orientation of the mirror 302, the central axis 322 thereof intersects the imaginary plane 330 at a separate one of a plurality of intersection locations 332 on the imaginary plane 330. As shown by the three different iterations in FIGS. 3A-3C, for each different orientation of the mirror 302 and thus different intersection location 332a, 332b, 332c of the central axis 322 with the imaginary plane 330, light from the laser unit 206 will be reflected from the reflective surface 320 of the mirror 302 at a different angle towards the flow cell of the cell unit 208. Thus, reflected light from the laser unit 206 enters the focusing lens (not shown in FIGS. 3A-3C) at a different angle for each orientation of the mirror 302 resulting in the light being focused by the focusing lens at a different spot in the flow cell of the flow cell unit 208. In this regard, rotation of the mirror 302 around its tip axis 304 may correspond with positioning of the focused light in a vertical (up and down) direction, and rotation of the mirror 302 around its tilt axis 304 may correspond with positioning of the focused light in a horizontal (left and right) direction.

Figure 4:
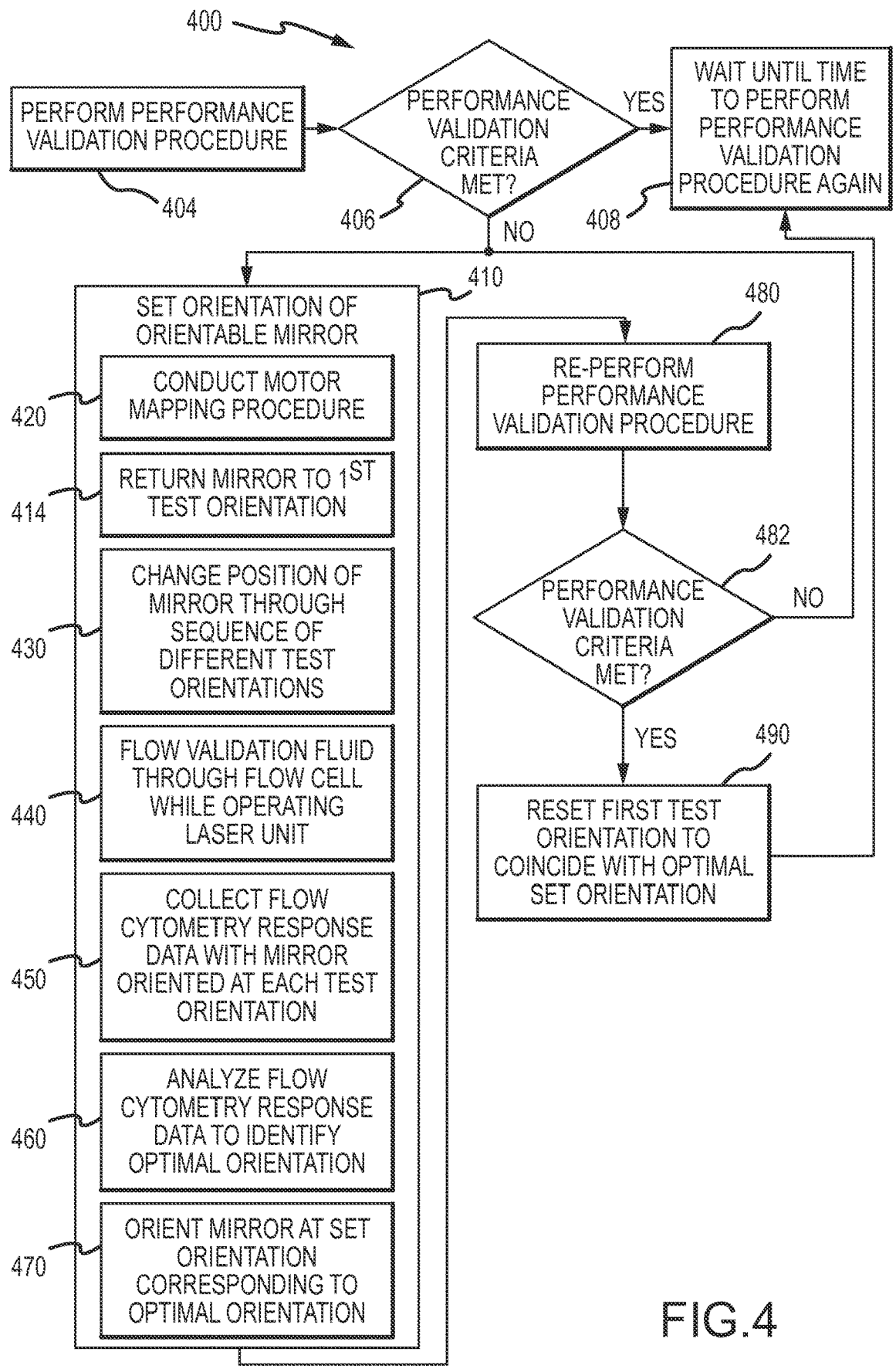
FIG. 4 is a flow diagram depicting the steps of one embodiment of a method of aligning a light path to direct light from a light source to a flow cell of a flow cytometer instrument.

FIG. 4 illustrates steps that may be included in a method 400 of aligning a light path to direct light from a light source to a flow cell of a flow cytometer instrument. In one implementation, the method 400 may be applied to a flow cytometer instrument such as flow cytometer 100 of FIGS. 1A-1B having a flow cytometer internal assembly 180 such as depicted in FIGS. 2A-2D to achieve alignment of the first optical path 250 in order to optimize application of excitation light from the laser unit 206 into the flow cell of the flow cell unit 208.

Execution of method 400 may be prompted by an outcome of step 404 in which a performance validation procedure is performed on the flow cytometer instrument. The performance validation procedure may be initiated by a user of the flow cytometer instrument (e.g., after being prompted to do so by a notification displayed by the instrument) and/or the performance validation procedure may be automatically run at regular intervals. The performance validation procedure of step 404 may include operating the flow cytometer instrument to perform a test flow cytometer investigation on a validation standard fluid and comparing results of the test flow cytometry investigation with minimum performance validation criteria. As depicted in decision block 406, if the performance validation criteria are met, then the subsequent steps 410 etc. of method 400 are not undertaken as alignment of the light path is not necessary at such time. Rather, the performance validation procedure is performed again after waiting 408 a period of time. If the performance validation criteria are not met, then subsequent steps of method 400 may be performed.

The method 400 includes step 410 in which the orientation of the orientable mirror 302 is set. Step 410 may be initiated with step 414 in which the mirror 302 is returned to a first test orientation. In this regard, the first test orientation of the mirror 302 may initially be determined during a quality control process undertaken as part of manufacturing the flow cytometer instrument, and, as described further herein, reset as part of method 400. Step 414 in which the mirror 302 is returned to the first test orientation may involve operating one or both of the motors 270, 272 coupled to the mirror 302 to return the mirror 302 to the first test orientation.

In step 420, a motor mapping procedure may be conducted to obtain a current absolute mirror 302 orientation. The motor mapping procedure of step 420 may be performed before returning the mirror 302 to its first test orientation. In one implementation where the motors 270, 272 that control the orientation of the mirror 302 are linear stepper motors, the motor mapping procedure 420 may proceed by operating each motor 270, 272 until it has reached a minimum limit of the motor 270, 272 and operating each motor 270, 272 until each motor 270, 272 has reached a maximum limit of the motor 270, 272 while counting the number of steps of each motor 270, 272 between the minimum limit and the maximum limit of the motor 270, 272.

In step 430, starting with the mirror 302 in its first test orientation, the position of the orientable mirror 302 is changed from the first test orientation through a sequence of different test orientations. In this regard, one or both of the linear stepper motors 270, 272 may be operated to change the orientation of the mirror 302 from the first test orientation to each of the different test orientations in the sequence. When operating one or both of the motors 270, 272 to change the orientation of the mirror 302 (e.g., when returning it to the first test orientation in step 414 or moving it through the sequence of different test orientations in step 430), a motor backlash parameter associated with each of the motors 270, 272 may be applied each time one of the motors 270, 272 reverses direction (e.g., when the motor 270, 272 switches between extending and retracting its output shaft) to compensate for small discontinuities in the response of the mirror orientation to movement of the motor 270, 272 upon reversal. The motor backlash parameter associated with each motor 270, 272 may be established through testing of the motors 270, 272 during manufacturing of the flow cytometer 100 and stored as a predetermined parameter in a software module that controls operation of the motors 270, 272. The motor backlash parameter may vary from instrument to instrument and motor to motor.

In each test orientation of the sequence of different test orientations, the central axis 322 of mirror 302 intersects the imaginary plane 330 at a separate intersection location 332 on the imaginary plane 330. In this regard, the sequence of different test orientations may result in the intersection locations being in a uniformly spaced grid pattern on the imaginary plane.

Figure 5:
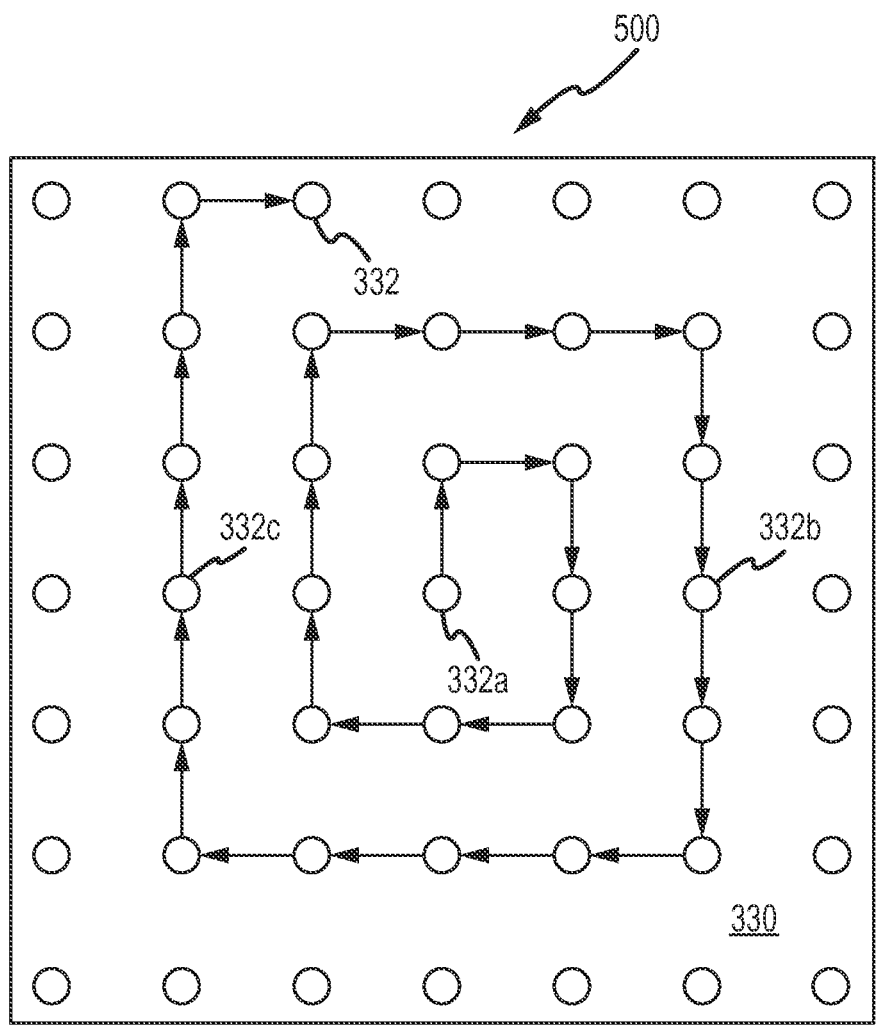
FIG. 5 depicts an exemplary uniform grid of intersection locations of a central axis of an orientable mirror with a plane.

For example, FIG. 5 shows an exemplary uniform grid 500 of intersection locations 332 on the imaginary plane 330 wherein the sequence of different test orientations of the mirror 302 results in a grid 500 centered around a first intersection location 332A associated with the first test orientation that is traversed in a fixed pattern. In one implementation, the fixed pattern by which the grid 500 of intersection locations is traversed as a result of the sequence of different test orientations of the mirror 302 may be an clockwise spiral outward from the first intersection location 332A as depicted in FIG. 5. In other implementations of the method 300, the fixed pattern by which the grid 500 is traversed may be a counter-clockwise spiral outward from the first intersection location 332A or even a manner other than spiraling outward from the first intersection location 332A. A clockwise or counter-clockwise fixed pattern may be desirable because such a pattern minimizes reversals in the direction of the motors 270, 272 used to change the orientation of the mirror, and thus minimizes the need to apply the motor backlash parameter.

In step 440, for each test orientation in the sequence, a validation fluid is flowed through the flow cell of the flow cell unit 208 while the laser unit 208 is operated to provide light to the mirror 302. The light from the laser unit 206 is reflected by the reflective surface 320 of the mirror 302 to the focusing lens 216 which focuses the light at a spot on the flow cell of the flow cell unit 208 corresponding with the particular test orientation in which the mirror 302 is oriented. The validation fluid comprises a known concentration of at least one known particle.

In conjunction with step 440, in step 450, flow cytometry response data is collected on light emitted from the flow cell of the flow cell unit 208 with the mirror 302 oriented at each test orientation.

In step 460, the flow cytometry response data is analyzed to identify an optimal orientation of the mirror from among each of the test orientations of the mirror. Analysis of the flow cytometry response data may involve calculating a concentration level of at least one particle in the validation sample fluid from the flow cytometry response data for each test orientation of the mirror 302, and selecting the optimal orientation of the mirror from among the test orientations of the mirror based at least in part on the calculated concentration level of the at least one particle for each test orientation of the mirror 302.

In one implementation, selection of the optimal orientation of the mirror may include calculation of one or more additional metrics from the flow cytometry response data for each test orientation of the mirror in addition to the calculated concentration level of the at least one particle. In this regard, the additional metrics may include an average signal peak height of the time series signal data trace corresponding with each test orientation of the mirror. The calculated concentration levels and the additional metrics may be normalized and weighted. Each test orientation of the mirror may be listed in order of response quality based on the normalized and weighted calculated concentration levels and the additional metrics, with the optimal orientation being selected as the one with the highest response quality.

In step 470, the mirror 302 is oriented in a set orientation corresponding to the identified optimal orientation. In this regard, one or both of the linear stepper motors 270, 272 may be operated to position the mirror 302 oriented in accordance with the test orientation identified as being optimal.

In step 480, after the first optical path 250 has been aligned by orienting the mirror 302 in accordance with the set orientation, the performance validation procedure of step 404 may be re-performed. As depicted in decision block 482, if the performance validation criteria are now met, then the method 400 may proceed to step 490. If the performance validation criteria are not met after aligning the optical path, then method 400 may be undertaken again and/or a user of the flow cytometer instrument may be informed that the performance validation criteria have not been met.

In step 490, the first test orientation of the mirror 302 may be reset to coincide with the set orientation of the mirror 302. Thus, the next time that method 400 is undertaken, first test orientation of the mirror 302 will be in accordance with the optimal orientation as determined by method 400. With the physical orientation of the mirror 302 having thus been established, the flow cytometer instrument may now be operated to conduct a flow cytometry investigation on a sample fluid. Further, the performance validation procedure may be performed again after waiting 408 a period of time.

Figure 6:
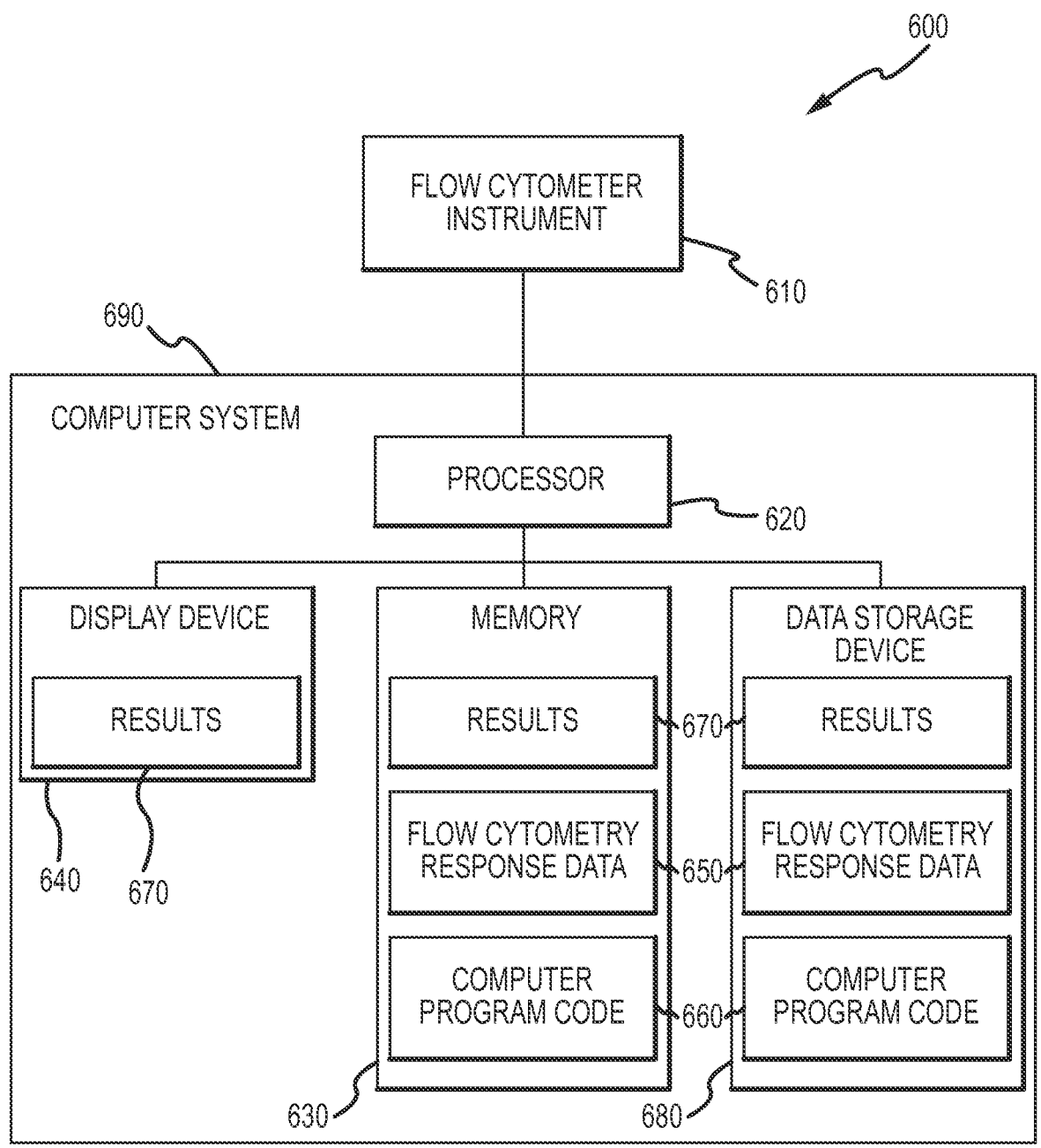
FIG. 6 is a block diagram of one embodiment of a flow cytometer system.

FIG. 6 is a block diagram representation of one embodiment of a flow cytometer system 600. The flow cytometer system 600 includes flow cytometer instrument 610, a processor 620, a memory 630 and a display device 640. The flow cytometer instrument 610 may, for example, comprise a flow cytometer instrument 100 having a flow cytometer internal assembly 180 within an enclosure 102 such as depicted and described in connection with FIGS. 1A-1B and 2A-2D. Regardless of its configuration, the flow cytometer instrument 610 is operable to output flow cytometry investigation response data 650, where the response data 650 comprises one or more time series signal data traces corresponding with detection during the flow cytometry investigation of light from the sample fluid in one or more wavelength ranges indicative of the presence of one or more particle attributes in a sample fluid undergoing flow cytometry investigation. The response data 650 may be stored in the memory 630. The processor 620 is operable to receive the flow cytometry response data 650 output by the flow cytometer instrument 610. In this regard, the processor 620 may receive the response data 650 directly from the flow cytometer instrument 610 as it is output and/or from the memory 630 where the response data 650 has been stored. The processor 620 is operable to process the response data 650 to, among other things, calculate a concentration level and/or an average signal peak height of the time series signal data traces. For example, the processor 620 may calculate a concentration level and/or an average signal peak height of a time series signal data trace for a known particle included in a validation sample fluid.

In order to ensure that the flow cytometer instrument 610 is achieving optimal performance, the processor 620 may be operable to regularly perform an automated alignment process such as method 400 of aligning a light path to direct light from a light source to a flow cell of the flow cytometer instrument 610 depicted and described in connection with FIG. 4. In this regard, the processor 610 may comprise a general purpose microprocessor, and computer executable program code 660 may be stored on the memory 630 and executed by the processor 620 to accomplish the steps of method 400. It may also be possible for the processor 620 to comprise one or more application specific integrated circuits (ASICs) and/or field programmable gate arrays (FPGAs) in combination with a general purpose microprocessor that together accomplish the steps of method 400 or one or more ASICs and/or FPGAs without a general purpose microprocessor that accomplish the steps of method 400. Results 670 of the automated alignment process 400 accomplished by the processor 620 may be displayed on the display device 640. The results 670 may be displayed as the automated alignment process 400 is ongoing and/or after it is completed. The results 670 may also be stored in the memory 630 and/or on a non-volatile data storage device 680 (e.g. a hard disc, an optical disc, a flash memory, etc.) that may be included in the flow cytometry system 600. In addition to storing the results 670, the non-volatile data storage device may also store the response data 650 and/or the computer executable program code 660. In one implementation such as depicted, the processor 620, memory 630, display device 640 and data storage device 680 comprise a computer system 690 separate from the flow cytometer instrument 610 and interfaced therewith for communication therebetween. In this regard, the computer system 690 may, for example, comprise a laptop, desktop, notebook, or touch pad computing device, and may have additional components not depicted such as a keyboard, mouse and/or touch screen/pad input device. In other implementations, one or more of the processor 620, memory 630, display device 640, and data storage device 680 may be incorporated within the flow cytometer instrument 610.

Deviations may be made from the specific embodiments disclosed in the specification without departing from the spirit and scope of the invention. For example, at least some of the functionalities performed by many of the processes, devices and modules etc. discussed herein may be performed by other modules, devices, processes, etc. The illustrations and discussion herein has only been provided to assist the reader in understanding the various aspects of the present disclosure.

Furthermore, the various utilities disclosed herein (e.g., the method of a method of aligning a light path to direct light from a light source to a flow cell of the flow cytometer instrument) are not limited to being used in the context of the specific flow cytometer instrument described herein.

A computer program (also known as a program, software, software application, script, or code) used to provide the functionality described herein (such as to provide one or more steps of the method of a method of aligning a light path to direct light from a light source to a flow cell of the flow cytometer instrument) may be written in any form of programming language, including compiled or interpreted languages, and may be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by an information flow network.

The block diagrams, processes, protocols and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Generally, the elements of a computer are a processor for performing instructions and one or more memory devices for storing instructions and data. The techniques described herein may be implemented by a computer system configured to provide the functionality described.

While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Additionally, the foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A flow cytometer system comprising:
a flow cell;
a light source;

a light path to direct light from said light source to said flow cell;

an orientable mirror disposed in the light path that directs light from the light source into the flow cell;

at least one detector that detects light from the flow cell; and a computer system with a control processor and programmed with computer program code executable by the processor to:

starting with the mirror positioned at a first test orientation, control the mirror to change positioning of the mirror in a test orientation pattern from the first test orientation through a sequence of different test orientations of the mirror following the first test orientation;

for each said test orientation of the mirror, control flowing of a validation fluid through the flow cell while the light source is operating to provide light to the mirror and collecting flow cytometry response data on light emitted from the flow cell with the mirror at the said test orientation, the validation fluid comprising a known concentration level of at least one known particle;

analyze the flow cytometry response data to identify an alignment orientation for the mirror, comprising calculating from the flow cytometry response data for each test orientation of the mirror a concentration level of the at least one particle in the validation fluid and selecting the alignment orientation of the mirror based at least in part on the calculated concentration level of the at least one particle for each test orientation of the mirror; and control the mirror to be at a set orientation corresponding to the identified alignment orientation to align the mirror with the light source along the light path.

2. A system according to claim 1, wherein:

the mirror has a reflective surface and a central axis extending perpendicular to the reflective surface, and at each said test orientation of the mirror, the central axis intersects a plane transverse to the light path between the mirror and the flow cell at a separate intersection location on the plane; and the sequence of different orientations of the mirror results in the intersection locations being in a uniformly spaced grid on the plane.

3. A system according to claim 2, wherein the uniformly spaced grid is centered around a first intersection location associated with the first test orientation of the mirror.

4. A system according to claim 3, wherein the uniformly spaced grid is traversed in a fixed pattern starting from the first intersection location.

5. A system according to claim 4, wherein the fixed pattern minimizes reversals of the direction in which one or more motors coupled to the mirror are operated to change the orientation of the mirror from the first test orientation to each of the different test orientations of the mirror.

6. A system according to claim 4, wherein the fixed pattern comprises one of a clockwise and a counter-clockwise pattern spiraling outward from the first intersection location.

7. A system according to claim 4, further comprising:

one or more motors coupled to the orientable mirror, wherein said one or more motors are in communication with said processor and the computer system is programmed with the computer program code executable by the processor to return the mirror to the first test orientation of the mirror and to change the orientation of the mirror from the first test orientation to each of the different test orientations of the mirror.

8. A system according to claim 7, wherein said computer system is programmed with the computer program code executable by the processor to conduct a motor mapping procedure to obtain a current absolute mirror orientation.

9. A system according to claim 8, wherein the motor mapping procedure is conducted prior to operating said one or more motors coupled to the orientable mirror to return the mirror to the first test orientation.

10. A system according to claim 8, wherein each of said one or more motors comprises a linear stepper motor to drive linear motion steps, and wherein said computer system is programmed with the computer program code executable by the processor to conduct the motor mapping procedure by:

operating each of said one or more motors until each motor has reached a minimum linear position limit of the motor;

operating each of said one or more motors until each motor has reached a maximum linear position limit of the motor; and counting the number of linear motion steps of each of said one or more motors between the minimum linear motion limit and the maximum linear motion limit of the motor.

11. A system according to claim 10, wherein each said linear motion step of each of said one or more motors corresponds to no more than 300 nanometers of linear motion.

12. A system according to claim 7, wherein said computer system is programmed with the computer program code executable by the processor to apply a motor backlash parameter associated with each of said one or more motors when said each of said one or more motors reverses direction.

13. A system according to claim 1, wherein said computer system is programmed with the computer program code executable by the processor to analyze the flow cytometry response data to identify the alignment orientation of the mirror by:

for each test orientation of the mirror, calculating one or more additional metrics from the flow cytometry response data in addition to the calculated concentration level of the at least one particle;

normalizing and weighting the calculated concentration levels and the additional metrics; and listing each test orientation of the mirror in order of response quality based on the normalized and weighted calculated concentration levels and the additional metrics.

14. A system according to claim 13, wherein the additional metrics include an average signal peak height of the time series signal data trace corresponding with each test orientation of the mirror.

15. A system according to claim 1, wherein the mirror is rotatable around two axes of rotation to achieve each test orientation of the mirror.

16. A system according to claim 15, wherein:

a first one of the two axes of rotation comprises a tip axis of the mirror correlated with positioning of the light from the light source and reflected from the mirror in a first direction relative to the flow cell; and a second one of the two axes of rotation comprises a tilt axis of the mirror correlated with positioning of the light from the light source and reflected from the mirror in a second direction relative to the flow cell.

17. A system according to claim 16 wherein the first direction comprises a vertical direction and the second direction comprises a horizontal direction.

18. A system according to claim 1, wherein said computer system is programmed with the computer program code executable by the processor to:
   reset the first test orientation of the mirror to coincide with the alignment orientation of the mirror.

* * * * *